US009044535B2

(12) United States Patent
Garzaniti et al.

(10) Patent No.: US 9,044,535 B2
(45) Date of Patent: Jun. 2, 2015

(54) EXTRACORPOREAL BLOOD PUMP WITH DISPOSABLE PUMP HEAD PORTION HAVING MAGNETICALLY LEVITATED IMPELLER

(75) Inventors: Erin Jessica Lindsay Garzaniti, Ann Arbor, MI (US); Eric L. Gay, Ann Arbor, MI (US)

(73) Assignee: Terumo Cardiovascular Systems Corp., Ann Arbor, MI (US)

(*) Notice: Subject to any disclaimer, the term of this patent is extended or adjusted under 35 U.S.C. 154(b) by 2077 days.

(21) Appl. No.: 12/178,759

(22) Filed: Jul. 24, 2008

(65) Prior Publication Data
US 2009/0041595 A1 Feb. 12, 2009

Related U.S. Application Data

(60) Provisional application No. 60/963,841, filed on Aug. 7, 2007.

(51) Int. Cl.
 F04B 35/04 (2006.01)
 A61M 1/10 (2006.01)
 F04D 13/06 (2006.01)

(52) U.S. Cl.
 CPC ........... *A61M 1/101* (2013.01); *F04D 13/0666* (2013.01); *A61M 1/1015* (2014.02); *A61M 1/1031* (2014.02)

(58) Field of Classification Search
 CPC .................................................. F04D 13/0666
 USPC ............................ 417/356, 420, 423.1, 423.7
 See application file for complete search history.

(56) References Cited

U.S. PATENT DOCUMENTS

| | | | |
|---|---|---|---|
| 4,540,351 A * | 9/1985 | Olson | 417/476 |
| 5,575,630 A | 11/1996 | Nakazawa et al. | |
| 5,947,703 A * | 9/1999 | Nojiri et al. | 417/420 |
| 6,351,048 B1 | 2/2002 | Schob et al. | |
| 6,547,530 B2 | 4/2003 | Ozaki et al. | |
| 6,575,717 B2 | 6/2003 | Ozaki et al. | |
| 6,589,030 B2 | 7/2003 | Ozaki | |
| 6,623,475 B1 | 9/2003 | Siess | |
| 6,626,644 B2 | 9/2003 | Ozaki | |
| 6,840,735 B2 | 1/2005 | Yaegashi et al. | |

(Continued)

OTHER PUBLICATIONS

J. X. Shen, et al, A Novel Compact PMSM with Magnetic Bearing for Artificial Heart Application, IEEE Transactions on Industry Applications, vol. 36, No. 4, Jul./Aug. 2000, pp. 1061-1068.

(Continued)

*Primary Examiner* — Charles Freay
(74) *Attorney, Agent, or Firm* — Gael Diane Tisack, Esq.; Darryl Newell; MacMillan, Sobanski & Todd

(57) ABSTRACT

A pump drive unit has an openable housing that accommodates a disposable impeller unit which is pre-connected with tubing, while maintaining the tight tolerances and close spacing. A levitation system (magnets and sensors), drive motor and drive magnets, and control electronics are all re-usable and housed within relatively permanent structures. In one embodiment, a hinged top separates the levitating magnets to allow the impeller unit to be captured and retained with positional accuracy and in close proximity to the desired locations when the hinged top is closed. The top may be separated into sections covering unequal arcs to coincide with the organization of the magnetic subcomponents in the upper drive unit housing.

13 Claims, 10 Drawing Sheets

(56) References Cited

U.S. PATENT DOCUMENTS

| | | | |
|---|---|---|---|
| 7,033,147 B2 | 4/2006 | Yanai et al. | |
| 7,128,538 B2 * | 10/2006 | Tsubouchi et al. | 417/12 |
| 7,172,550 B2 | 2/2007 | Tsubouchi | |
| 7,980,835 B2 * | 7/2011 | LaBanco et al. | 417/477.12 |
| 2002/0094281 A1 * | 7/2002 | Khanwilkar et al. | 417/356 |
| 2005/0014991 A1 | 1/2005 | Sugiura | |
| 2005/0033232 A1 * | 2/2005 | Kriesel | 604/131 |
| 2005/0089422 A1 | 4/2005 | Ozaki et al. | |

OTHER PUBLICATIONS

Levitronix, CentriMag Ventricular Assist System, PL-0023 Rev. 00, 2003.

Levitronix, Ultra Clean Handling of Pure and Delicate Fluids, Th-Nov. 2003.

* cited by examiner

EXTRACORPOREAL BLOOD PUMP WITH DISPOSABLE PUMP HEAD PORTION HAVING MAGNETICALLY LEVITATED IMPELLER

CROSS REFERENCE TO RELATED APPLICATIONS

This application claims priority to U.S. provisional application Ser. No. 60/963,841, filed Aug. 7, 2007.

STATEMENT REGARDING FEDERALLY SPONSORED RESEARCH

Not Applicable.

BACKGROUND OF THE INVENTION

The present invention relates in general to centrifugal pumps for pumping blood in an extracorporeal blood circuit, and, more specifically, to a pump with a magnetically levitated impeller and with disposable and reusable portions that is applicable to blood pumps for short-term heart assist, especially following heart surgery.

During cardiac bypass surgery, if a patient's heart is slowed or stopped for surgical repair, his or her blood must be artificially oxygenated and pumped through the body using an extracorporeal support circuit. Using this system, venous blood is diverted from entering the right chambers of the heart and is instead directed through a series of tubes, pumps, and filters, which provide fresh oxygen to the blood and return it to the body's systemic circulation at the aorta. The oxygenated blood is then circulated throughout the body. The circuit thus ensures that the patient continues to be nourished by oxygenated blood flow while the heart is unable to function.

In performing such a procedure, a complicated apparatus is required. One or two blood reservoirs, an oxygenator (possibly combined with a heat exchanger), a blood pump, and multiple tubes to connect the various components are needed and must be assembled and arranged before surgery may begin. Typically a significant amount of time must be spent just prior to surgery to accomplish the set-up, and great attention must be paid to the details of this complicated task. In order to ease this task, a nearly complete support circuit is often assembled by the manufacturer in a sterile condition and packaged in a manner that protects sterility until the time that it is needed for a procedure. An assembly pack having a frame for supporting the individual disposable processing elements (e.g., filters, pump, oxygenator) and the interconnecting tubing is shown in U.S. Pat. No. 6,811,749, which is incorporated herein by reference in its entirety. Such a frame pack provides for quick set-up and integration into a complete extracorporeal support system, thus enhancing operating room efficiency.

Most of the components of the extracorporeal blood circuit are disposed of following the surgical procedure as medical waste since they have been exposed to the blood of the patient. Even relatively more expensive components such as a centrifugal pump are disposed of because the difficulty and cost of re-sterilization would be too great.

Centrifugal blood pumps are increasingly used in artificial heart/lung units for extracorporeal blood circulation. Centrifugal pumps of the magnetic coupling type wherein a driving torque from an external motor is transmitted to an impeller through magnetic coupling are commonly used because the physical communication between the blood chamber of the pump and the exterior can be completely excluded and invasion of bacteria is prevented. The centrifugal blood pump includes a chamber having a blood inlet port and a blood outlet port and an impeller rotatably accommodated in the housing to increase the difference between inlet and outlet fluid pressure by means of centripetal acceleration generated during its rotation. The impeller has one or more permanent magnets disposed thereon which are acted upon by attracting magnets of a drive motor that is disposed adjacent to the impeller chamber. Typically, the impeller rotates without contacting the housing by magnetically levitating above the bottom of the chamber. A separate set of levitating magnets that may include electromagnets is disposed axially and/or radially relative to the impeller in order to provide a precisely controlled levitating field. Position sensors are used to provide position feedback to a controller which drives the electromagnets. Tight tolerances and close distances between the impeller and the levitating magnets and sensors must be maintained in order to achieve proper pump functioning. Examples of magnetically levitated centrifugal blood pumps include U.S. Pat. Nos. 6,575,717; 6,589,030; 7,212,550; and 7,128,538, and U.S. patent application publication 2005/0014991 A1, all of which are incorporated herein by reference in their entirety.

It is often preferable to locate the levitating magnets and position sensors above (i.e., at the top of) the impeller chamber, opposite from the driving motor, especially when device volume is to be minimized, as in an implant application. However, with the impeller chamber sandwiched between other structures, it has not generally been segregated as a separate disposable element. Making a disposable impeller chamber (i.e., pump head) which is insertable into a nondisposable pump drive unit is especially difficult with drive components above and below the pump head, because of the desire to have all the tubing for the circuit pre-connected to the pump as part of a frame pack. Therefore, centrifugal pumps of this type have typically been used for long-term applications and have been disposed of with the rest of the hardware components.

SUMMARY OF THE INVENTION

The invention provides an openable pump drive unit housing that accommodates a disposable impeller unit which is pre-connected with tubing, while maintaining the tight tolerances and close spacing that are required when the unit is closed for use. The levitation system (magnets and sensors), drive motor and magnets, and control electronics are all re-usable and housed within relatively permanent structures. In one embodiment, a hinged top separates the levitating magnets to allow the impeller unit to be captured and retained with positional accuracy and in close proximity to the desired locations when the hinged top is closed. The top may be separated into sections covering unequal arcs to coincide with the organization of the magnetic subcomponents in the upper drive unit housing.

In one aspect of the invention, a blood pump comprises a disposable pump head having an inlet and an outlet formed in a sealed impeller unit housing. The pump head further comprises an impeller contained within the sealed impeller unit housing having a top disk and a bottom disk with impeller blades mounted therebetween. The top and bottom disks have respective magnetic structures. A re-usable levitation/drive unit is provided having relatively movable upper and lower housing sections. These housing sections are movable to an open position for allowing insertion of the disposable pump head and a closed position for retaining the disposable pump head in a predetermined position. The re-usable levitation/ drive unit includes a levitation magnet in one of the housing sections and a drive magnet in the other one of the housing sections.

DETAILED DESCRIPTION OF PREFERRED EMBODIMENTS

The invention utilizes a magnetic levitation (mag-lev) type of pump architecture as is used in the implantable DuraHeart® left ventricular assist system available from Terumo Heart, Inc., of Ann Arbor, Mich. Although it may be used in extracorporeal blood circuit applications, the control system for obtaining levitation and a desired rate of flow through the pump can be substantially similar to the known controller utilized in the DuraHeart® system. However, the present invention uses a plastic cassette for an impeller chamber with inlet and outlet ports and an internally-located plastic impeller disk with integral magnets to form a disposable impeller unit (i.e., blood pump). The disposable unit may be substantially disk-shaped about 3 inches in diameter and one inch tall. An increased pump impeller diameter over the implantable DuraHeart® version enables higher outlet pressure capability and overall size of the unit does not need to be minimized in the disposable application. The non-disposable components of the invention are contained in an openable housing so that the disposable unit is removable. The housing may open and close using different constructions, such as a sideways splittable top, a splittable and raisable top, and a clamshell, for example.

Figure 1:
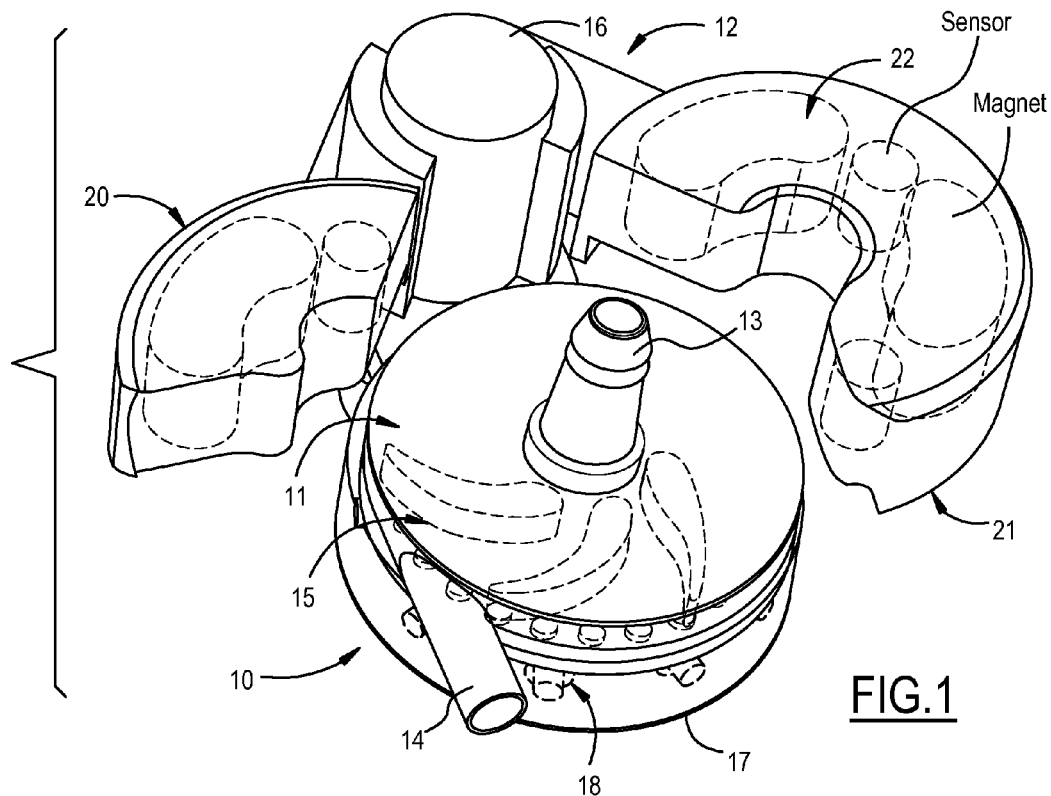
FIG. 1 is a top, perspective view of one embodiment of a pump system with a housing section opened and an impeller unit inserted.

Referring to FIG. 1, one embodiment of the invention includes a pump system 10 having a disposable impeller unit (or pump head) 11 and a re-usable levitation/drive unit 12. Impeller unit 11 has an inlet port 13, an outlet port 14, and an impeller section 15 which preferably includes a plurality of impeller blades. Levitation/drive unit 12 includes a support rod 16 to which its lower housing 17 is attached. Housing 17 contains a drive motor 18 which is driven by an externally generated motor drive signal from a controller (not shown). Drive motor 18 has a spinning rotor carrying a plurality of magnets that magnetically couple with magnets in the impeller section. Impeller unit 11 fits into lower housing 17 so that the spinning rotor and impeller section 15 are located in proper relationship. In this disposable device version, where external volume constraints are reduced, stronger driving electromagnets could be used than in an implantable version to enable greater separation between driving and driven magnets. This would allow thicker housing wall sections for a more robust and reliable pump head cassette.

Sideways jaws 20 and 21 hingedly extend from support rod 16 and contain an electronic assembly 22 that includes levitation magnets (both permanent magnets and electromagnets) and position sensors. Jaws 20 and 21 may comprise discrete magnets and sensors embedded within a plastic molded matrix. Alternatively, they could be fabricated using a layered material process to embed sensors and magnets and to construct wiring for electromagnets or signal transmission within a solid body, such as the Ultrasonic Consolidation technology used by Solidica, Inc., of Ann Arbor, Mich. This type of CNC-based fabrication provides advantages to the drive unit housing of added ruggedness, reliability, and overall physical integrity which are of high importance in a heart-assist device. Other advantages include precise locations of magnetic material, highly consistent magnetic fields, and improved consistency of unit-to-unit performance. The driving motor/rotor may also be fabricated in this way to obtain added precision of built-in magnetic regions.

Control electronics (e.g., for calculating and generating precisely determined currents needed within the various electromagnets to properly levitate the impeller section in vertical and axial center positions) may also be housed within jaws 20 and 21 or support rod 16, or they may be remotely located. In any case, a cable (not shown) is provided through rod 16 for supplying power. The cable may also carry operator command (e.g., pump speed) and/or other control signals.

Jaws 20 and 21 spread apart (e.g., rotate about rod 16) in order to provide space for impeller unit 11 to be placed within lower housing 17. Then jaws 20 and 21 are closed into an engaged position which captures inlet port 13 between jaws 20 and 21 and locates the levitating magnets and position sensors in a predetermined spatial relationship with impeller section 15. In addition to rotation in the plane perpendicular to rod 16 for spreading apart, it may also be desirable to provide for movement of jaws 20 and 21 or certain components thereof up and down (along the longitudinal axis of rod 16) so that they can be clamped in precise and close proximity to impeller unit 11 when in the closed position. Up/down and sideways motions can be used simultaneously so that jaws 20 and 21 follow slanted paths by providing appropriate cam surfaces within the supporting hinges in rod 16. These hinge and translation combinations can also be combined with various rigid linkages to better control both the elevated/offset and lowered/locked positioning of jaws 20 and 21 in the interest of minimizing impeller unit 11 installation time and effort.

The levitating magnets and sensors contained within jaws 20 and 21 are deployed around 360° with respect to the central rotational axis of the impeller. Individual electromagnets each occupy a respective arcuate segment of the 360° total and are closely packed together with the position sensors. Typically, potential sites for separation points to allow the jaws to spread apart are not diametrically opposed (i.e., the jaws cannot be broken into two 180° segments. Instead, there is more likely a three-fold symmetry which allows the jaws to separate into 120°, 240° and smaller segments. With use of the current DuraHeart® levitation control electromagnet sub-assemblies, the preferred included angle for the smaller segment is 86°.

Figure 2:
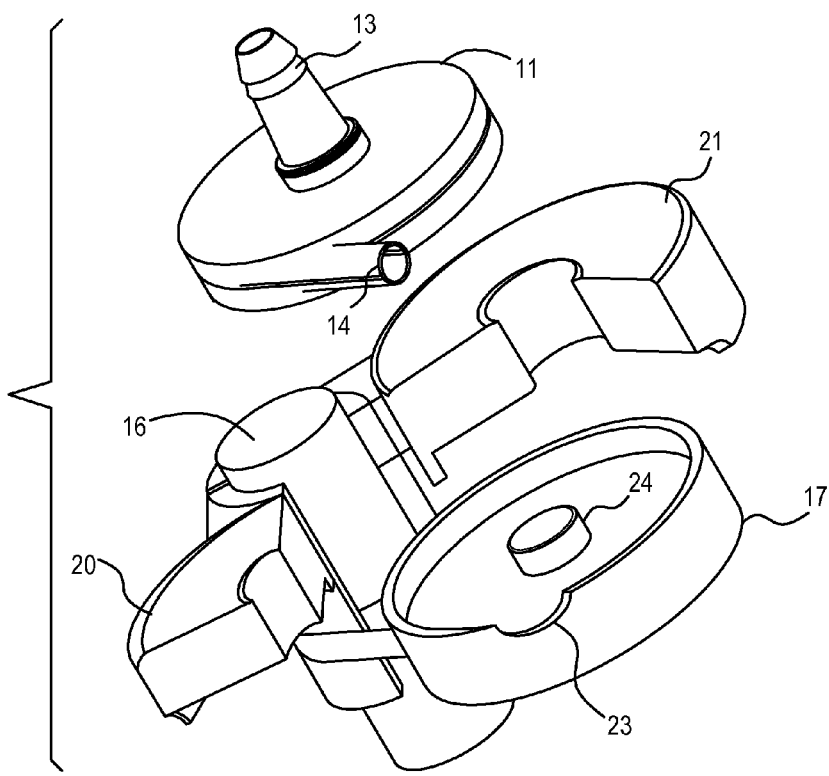
FIG. 2 is a side, perspective view of the pump system of FIG. 1 with the impeller unit removed from the housing section.
Figure 3:
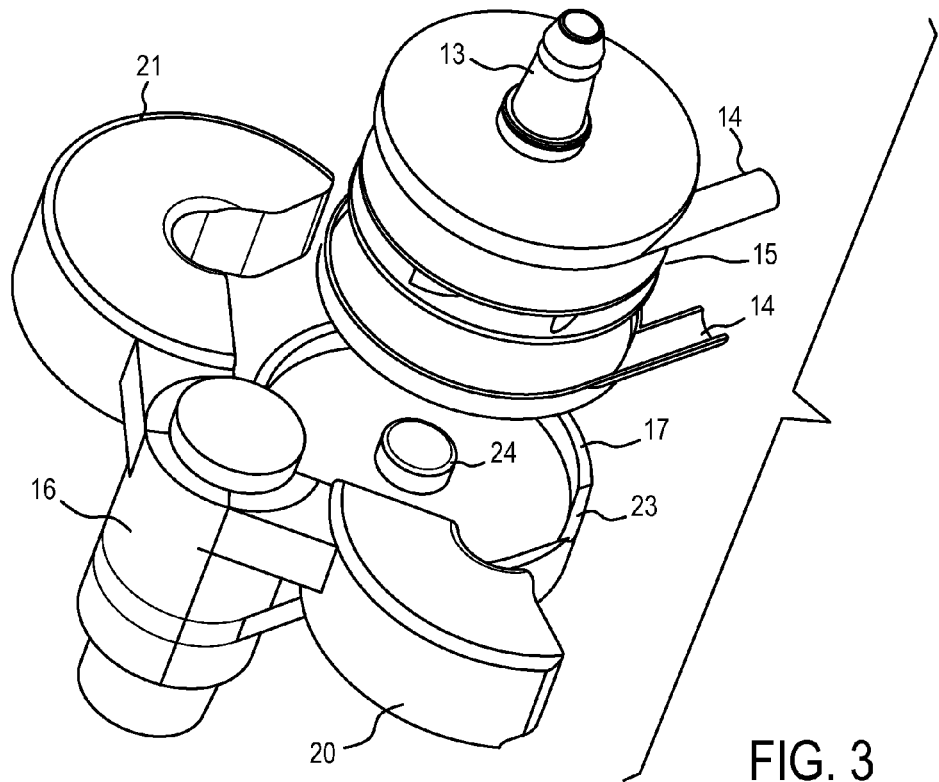
FIG. 3 is a rear, perspective view of the pump system of FIG. 1 with the impeller unit exploded.
Figure 4:
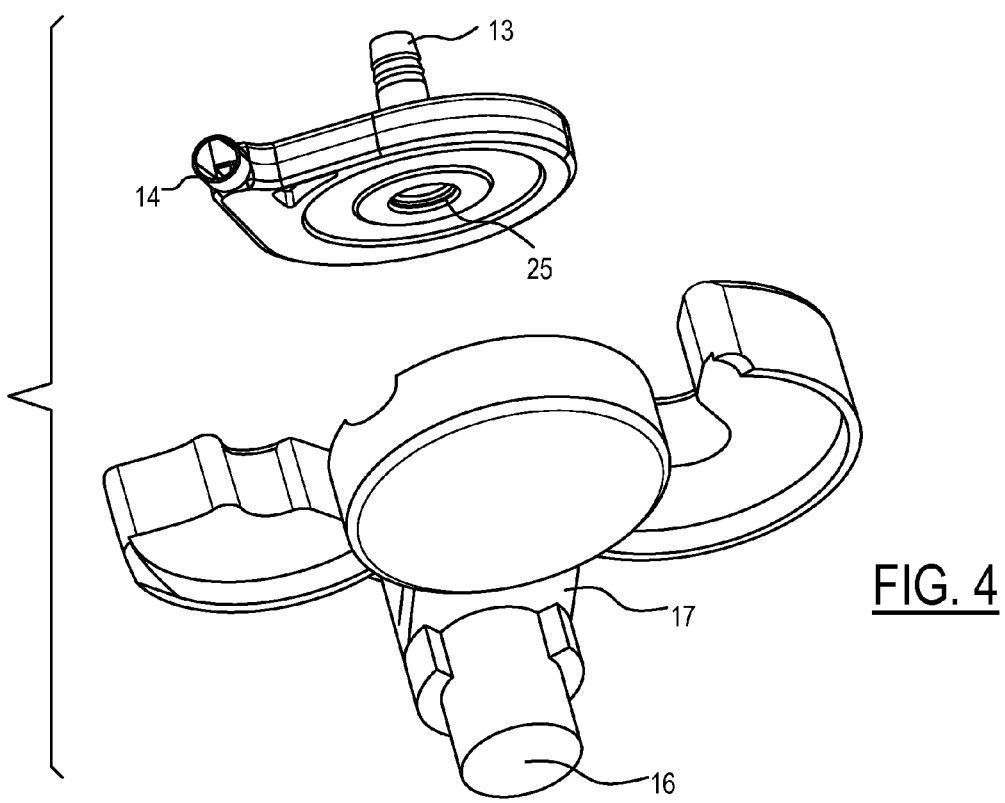
FIG. 4 is a bottom, perspective view of the pump system of FIG. 1.

FIGS. 2-4 show impeller unit 11 removed from lower housing 17. In order to fix impeller unit 11 in the proper orientation, a notch 23 formed in the side wall of lower housing 17 receives outlet port 14. In addition, a centrally-located post 24 raises from lower housing 17 to mate with a matching depression 25 in the bottom of impeller unit 11 which is coaxial with inlet port 13.

Figure 5:
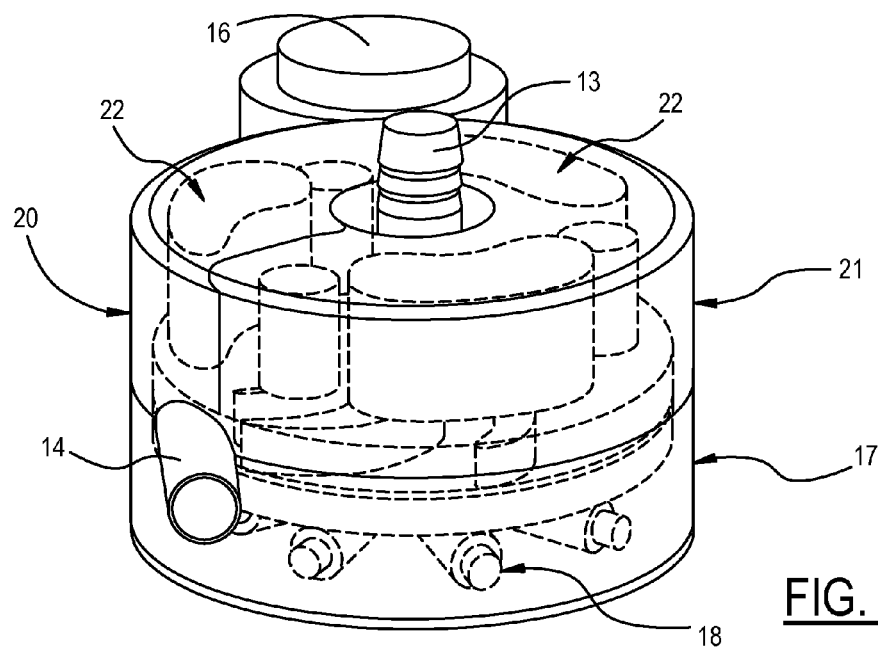
FIG. 5 is a front, perspective view with the housing section closed.

FIG. 5 shows the pump system in a closed position with the impeller unit captured in position so that the necessary tight tolerances and close spacing between magnets are achieved.

Figure 6:
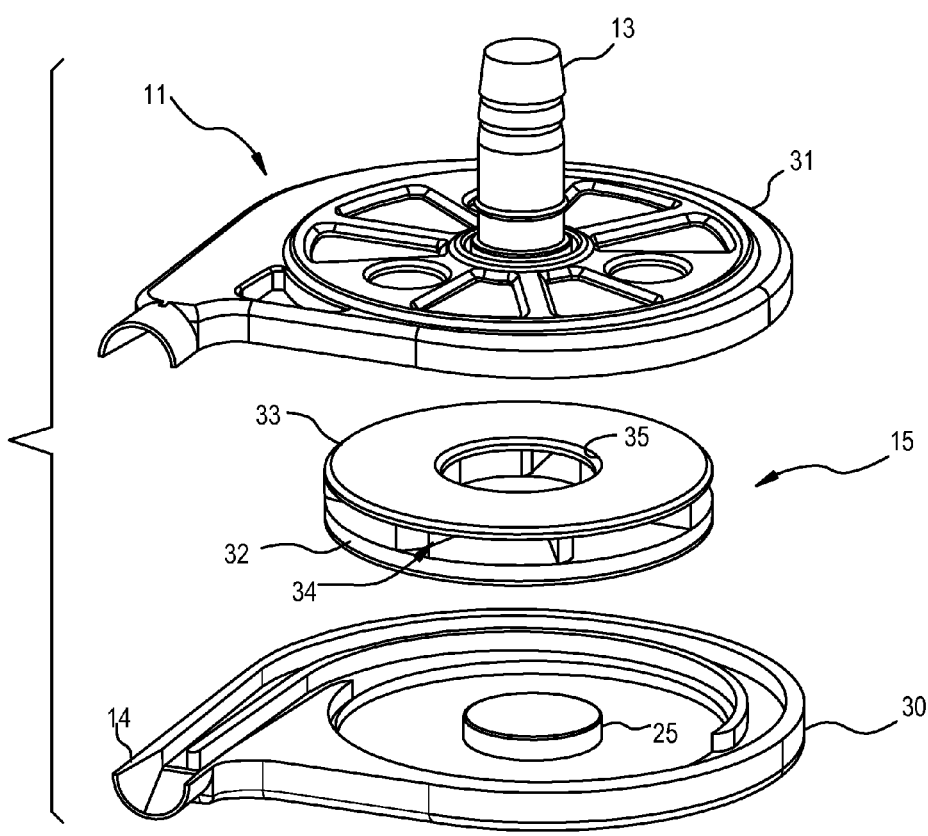
FIG. 6 is a top, perspective exploded view of an impeller unit (pump head).

FIG. 6 shows a top, front, perspective exploded view of impeller unit 11. A bottom cover 30 and a top cover 31 are joined to create an impeller pumping chamber for retaining impeller section 15. Impeller section 15 includes bottom and top disks 32 and 33 with a plurality of impeller blades 34 disposed therebetween. A hole 35 in disk 33 distributes blood from inlet port 13 to impeller blades 34. When impeller blades 34 are rotated about the impeller central axis, they generate a radial pressure gradient that produces a pressurized blood flow between inlet port 13 and outlet port 14.

Impeller section 15 is preferably levitated by interaction of an external magnetic field with magnetic structures in top disk 33, and is preferably rotated by interaction of another external magnetic field with magnets in bottom disk 32. More specifically, attraction to a levitating magnetic field generated in the upper housing levitates impeller section 15. A motor-driven circular array of magnets within the lower housing section transfers rotational energy to impeller section 15 by attraction/repulsion coupling with the magnets in bottom disk 32. Other arrangements are also possible.

Figure 7:
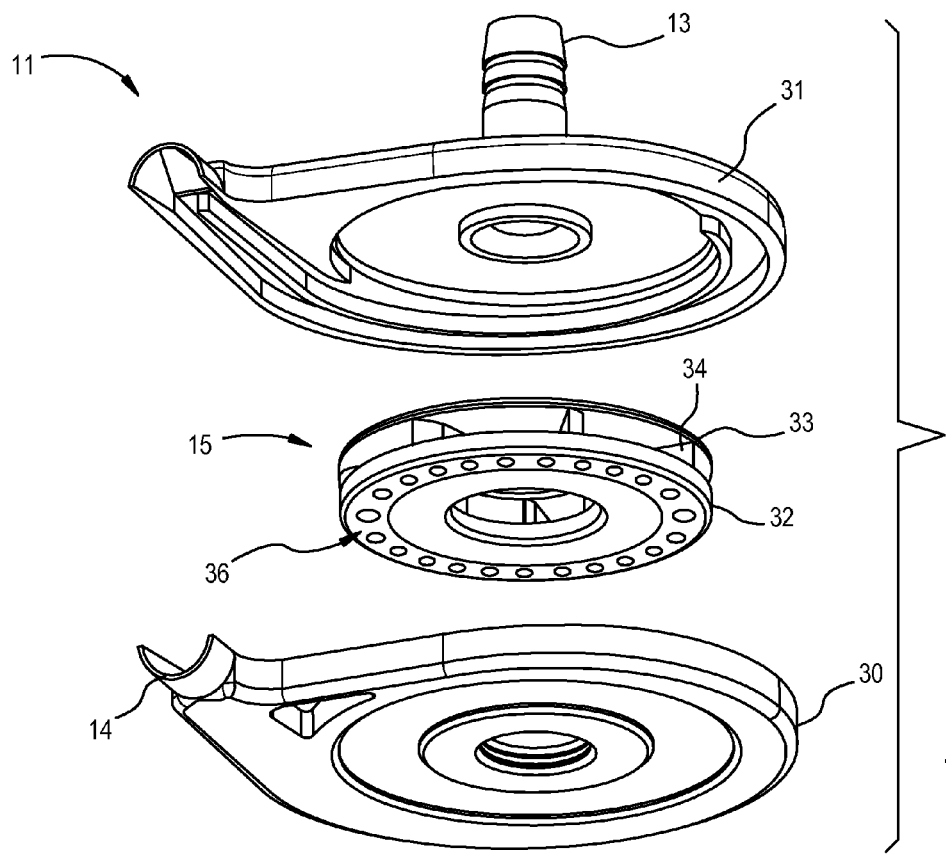
FIG. 7 is a bottom, perspective exploded view of a pump head.

FIG. 7 shows a bottom, front, perspective exploded view of impeller unit 11. Bottom disk 32 has a plurality of permanent magnets 36 mounted (e.g., glued) around the periphery of its bottom side or embedded within disk 32 by integral molding. They are preferably glued or embedded in such a manner that adjacent magnets have alternating magnetic polarities all the way around the periphery. In this embodiment, magnets on a rotor driven by the drive motor interact with magnets 36 from below in order to cause impeller section 15 to also rotate.

Figure 8:
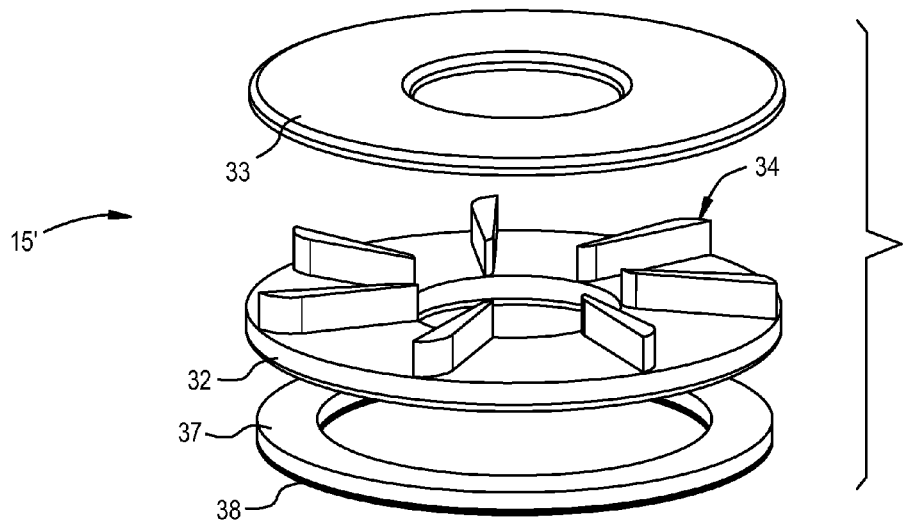
FIG. 8 is a top, perspective exploded view of an impeller section.
Figure 9:
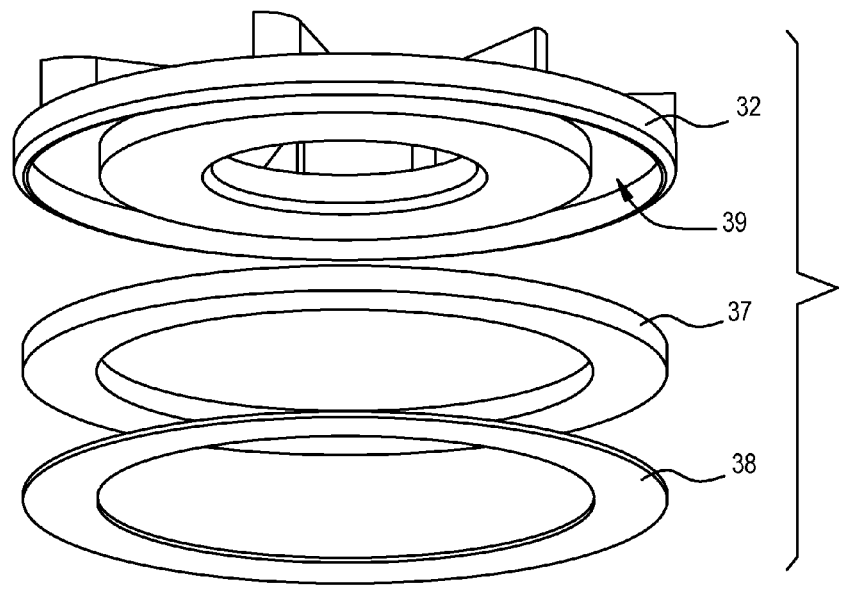
FIG. 9 is a bottom, perspective view of the exploded impeller of FIG. 8.

FIGS. 8 and 9 show an alternative embodiment of impeller section 15'. Top disk 33 is preferably formed separately from blades 34 and is adhesively bonded to them. Blades 34 may be integrally molded with bottom disk 32 or they may be welded or adhesively bonded in place. A magnet ring 37 is mounted in a toroidal recess 39 formed on the lower side of bottom disk 32 and is retained in recess 39 by a cover plate 38. Magnet ring 37 may have separate magnet pieces (not shown) glued to it or embedded within it, for example. Cover plate 38 may be glued or welded to bottom disk 32.

Figure 10:
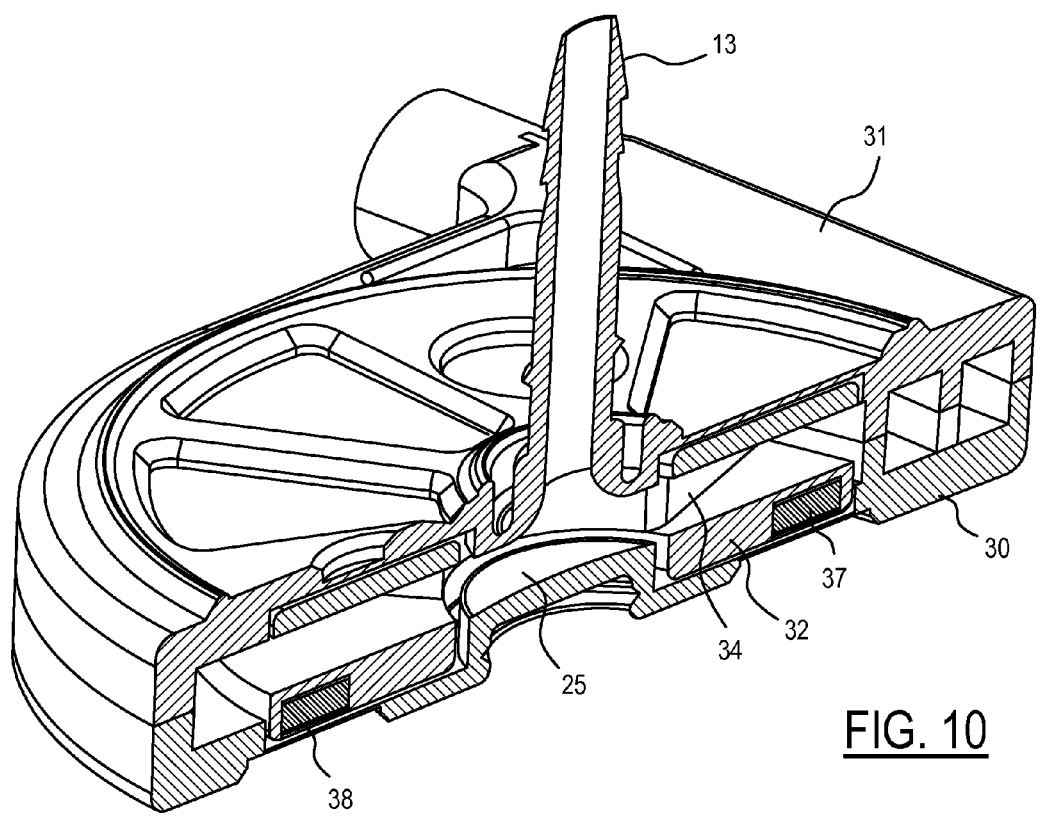
FIG. 10 is a cross-sectional view through the pump head.

FIG. 10 is a vertical cross section through the housing and pump head wherein the impeller section is constructed according to the embodiment of FIGS. 8 and 9.

Figure 11:
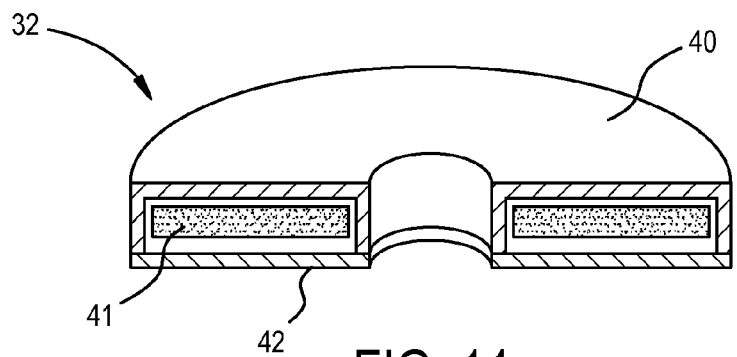
FIG. 11 is a cross-sectional view through an alternative embodiment of a bottom disk and magnet portion of the impeller section.
Figure 12:
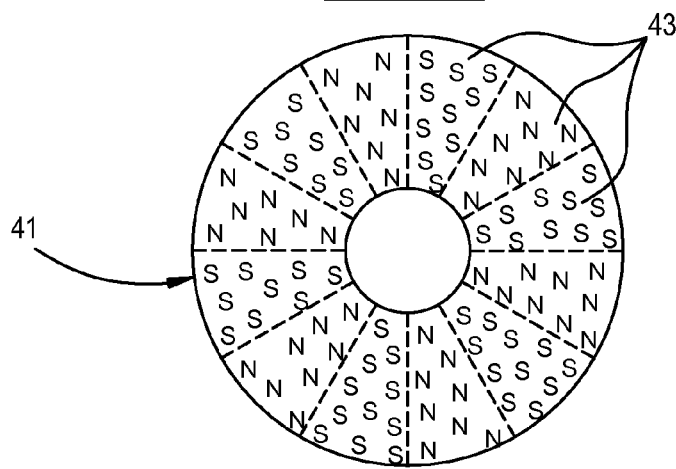
FIG. 12 is a top view of the magnet disk of FIG. 11.

FIG. 11 shows an alternative embodiment for bottom disk 32 wherein the magnets are formed in a continuous disk made of a magnetic material with appropriate magnetic domains formed within it. Thus, a toroidal plastic channel 40 is shown in cross section receiving a magnet disk 41. A cover 42 is joined (e.g., glued or ultrasonically welded) to channel 40 so that magnet disk 41 is captured in place. Magnet disk 41 is preferably formed of a molded magnetic material such as fine grained rare earth (e.g., neodymium) magnetic material in a plastic matrix. The magnetic particles are present throughout the disk and are initially magnetized in random directions. Permanently magnetized areas 43 as shown in FIG. 12 are produced by applying high-flux magnetic fields to the disk while located in a fixture (e.g., containing electrodes energized by capacitive discharges so that strong, precisely located permanent magnetic fields having the desired polarity are created in disk 41).

Figure 13:
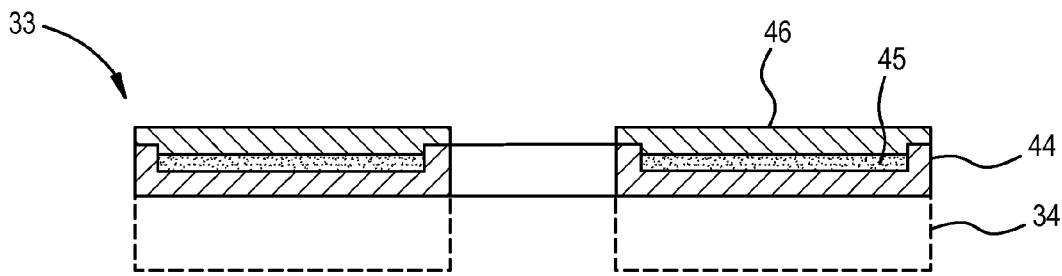
FIG. 13 is a cross-sectional view through an embodiment of the top disk of an impeller section including a magnet portion.
Figure 14:
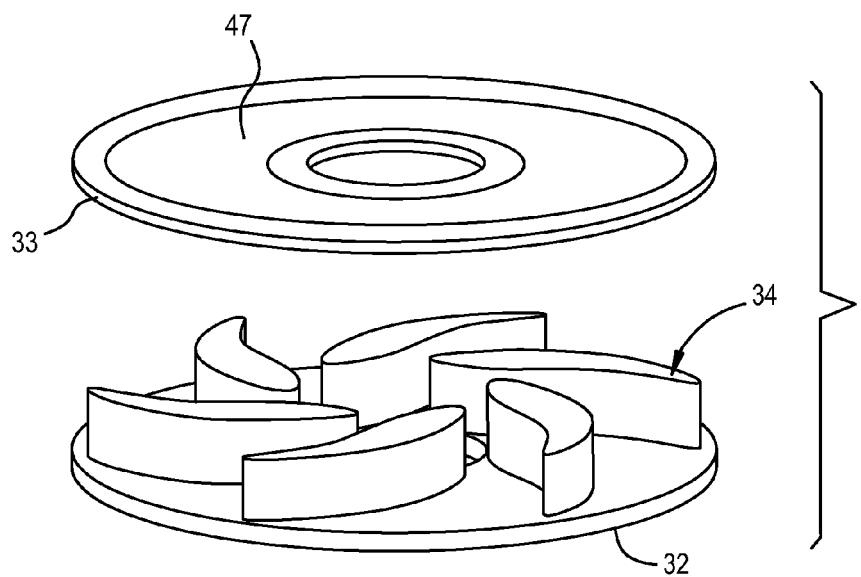
FIG. 14 is an exploded view of an alternative embodiment of an impeller section.

FIG. 13 shows a cross section of one embodiment of top disk 33. As is known in the art, it is desirable to create a uniform levitating magnetic field using a magnetic sheet at the top of the impeller. Thus, a circular plastic channel 44 receives a magnetic disk 45 that is locked in place by a cover 42. Disk 45 may comprise a metal sheet or may comprise a molded magnetic material having its magnetic domains appropriately oriented. Rather than being embedded within top disk 33, a magnetic disk 47 can be attached directly to top disk 33 as shown in FIG. 14.

Figure 15:
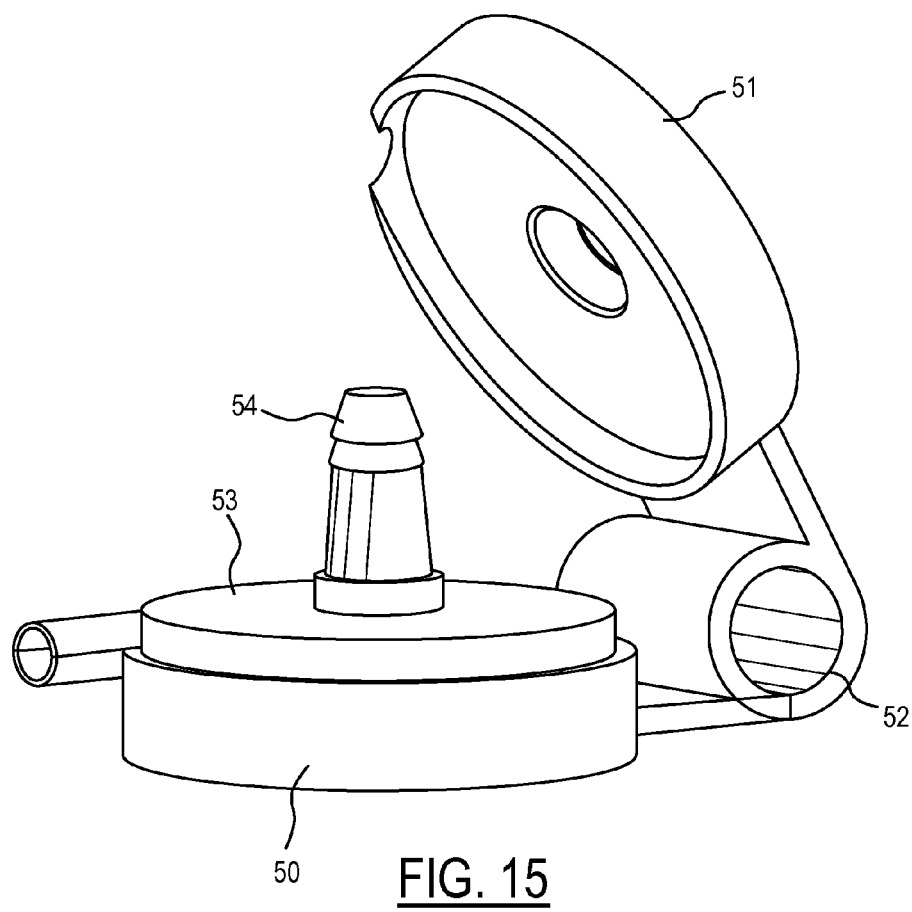
FIG. 15 is a side view of an alternative embodiment of the housing section in an open state.
Figure 16:
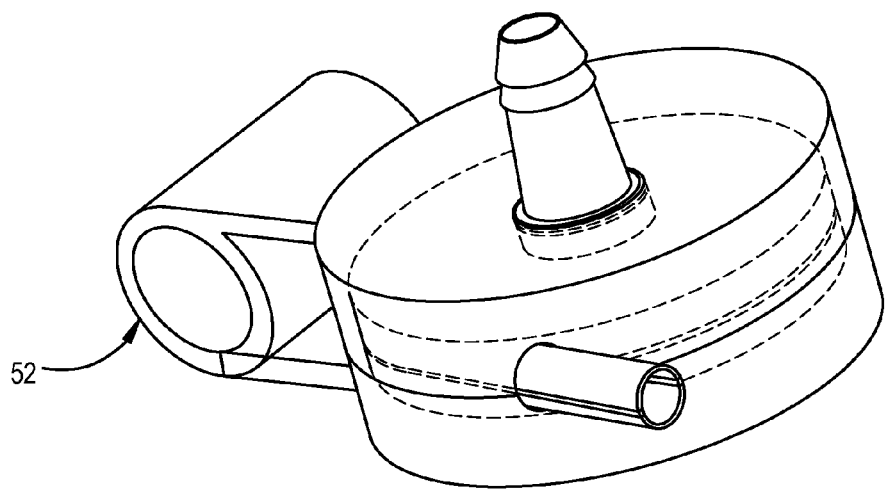
FIG. 16 is a perspective view of the pump system of FIG. 15 in a closed state.

FIGS. 15 and 16 show an alternative embodiment of the levitation/drive unit housing section using a re-usable clam shell housing to retain a disposable cassette (i.e., impeller unit). A lower clam shell 50 is joined to an upper clam shell 51 by a hinge 52. A disposable cassette 53 sets into lower clam shell 50 when the shell is in the open position (FIG. 15) and is clamped between lower and upper clam shells 50 and 51 when in the closed position (FIG. 16). Cassette 53 and lower clam shell 50 may have the same overall shapes as in the previous embodiments. Upper clam shell 51 may be a continuous ring since it receives inlet port 54 axially.

Figure 17:
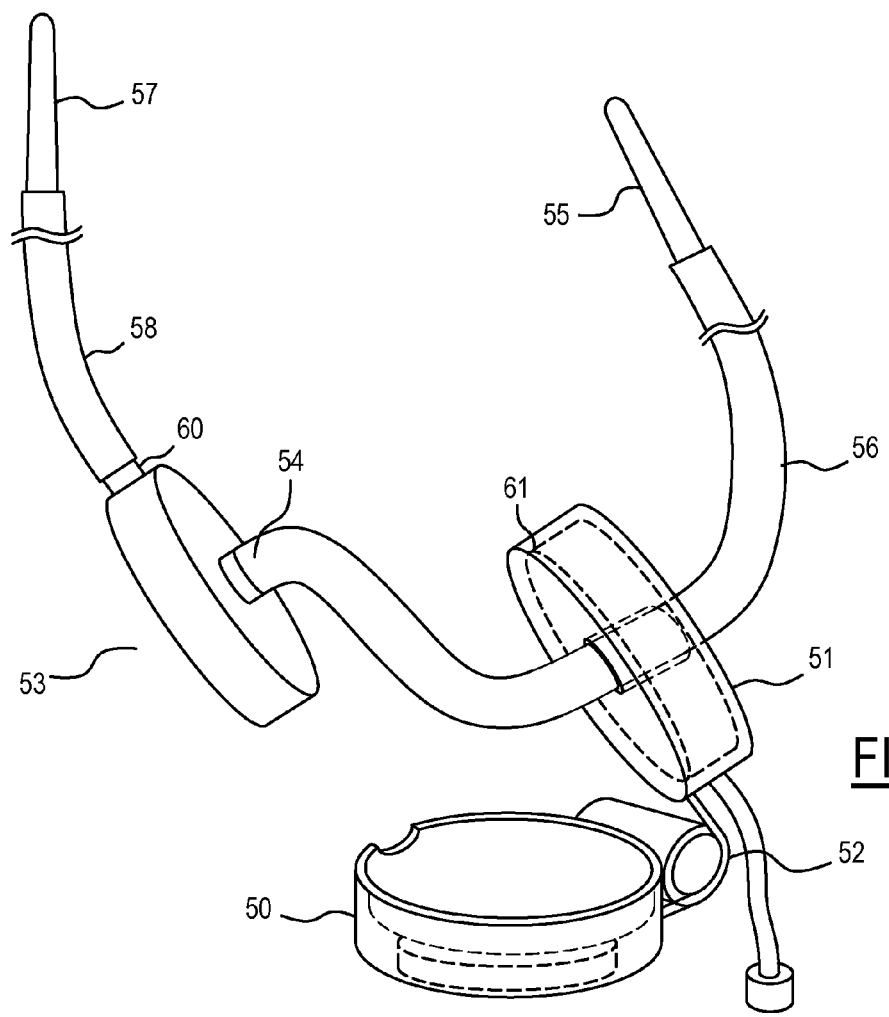
FIG. 17 shows a pump system pre-connected to tubing for an extracorporeal blood circuit.

The clam shell embodiment of FIGS. 15 and 16 does not accommodate a pump head cassette that is pre-installed with closed loop tubing of a frame pack, for example, because of the need to insert inlet port 54 axially through upper clam shell 51. However, a clam shell is useful in other applications of extracorporeal blood circuits, such as a temporary cardiac assist application as shown in FIG. 17. A venous cannula 55 for removing blood from a patient is coupled to inlet port 54 by a tube 56. An arterial cannula 57 is coupled by a tube 58 to pump outlet port 60. Since the tubing does not form a closed loop, cannula 55 and tube 56 can be "snaked" through the central hole in upper clam shell 51, and then cassette 53 can be closed between clam shells 50 and 51. Advantageously, a single latching/locking mechanism (not shown) can securely hold this type of assembly in its closed position. Disposable plastic shields can be provided on the clam shells, such as a shield 61 on upper clam shell 51, to protect them and their internal components from the sterile or post-use blood-contaminated cannulae. As represented in FIGS. 15 and 16, certain features of the pump head cassette, such as the outlet and associated housing details, tend to provide indexing features useful for proper rotational positioning within the drive unit housing. Features of this type may also be exaggerated axially and/or radially to better enable easier and more rapid pump system assembly. Alternatively, the drive unit housing may be modified to reduce or eliminate the need for pump head indexing to a preferred rotational position. Axial movement of magnet and sensor elements into close proximity with the impeller unit housing also provides lockdown security for the entire assembly, as the impeller unit becomes mechanically trapped in its operating position. This adds a type of attitude insensitivity to the overall operating unit, allowing rapid and secure placement into the desired location against or near the patient.

Figure 18:
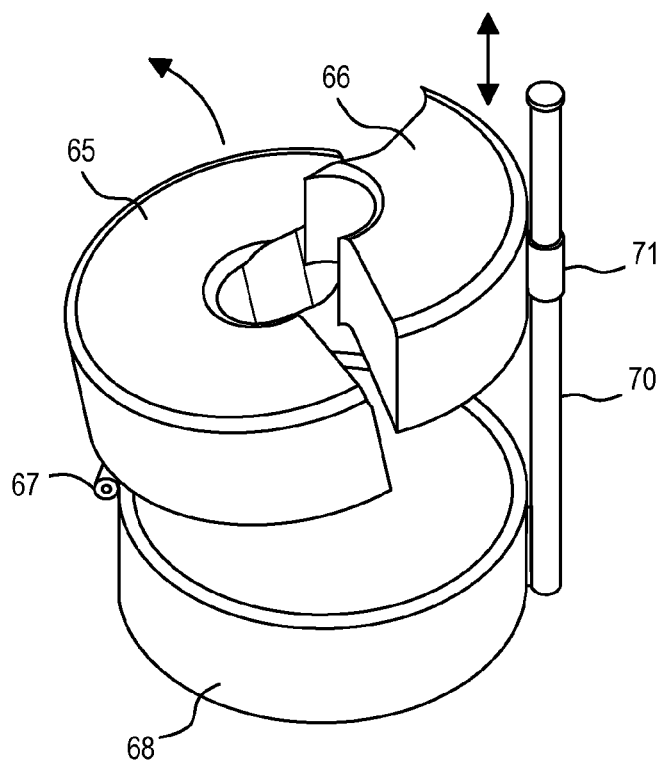
FIGS. 18-21 illustrate other alternative embodiments for providing an openable housing section.

FIG. 18 shows an embodiment wherein the top cover containing the levitation magnets and position sensors is separated into a section 65 and a section 66. Section 65 is attached by a hinge 67 to lower housing 68 so that section 65 rotates upward and away from lower housing 68 to allow insertion of the disposable impeller unit. A guide rod 70 extends vertically from lower housing 68 through a receiver 71 fixedly mounted to the side of section 66. Section 66 slides vertically upward so that the impeller unit can be installed or removed. A locking mechanism (not shown) may be provided to lock sections 65 and 66 in place when they are closed over the impeller unit.

Figure 19:
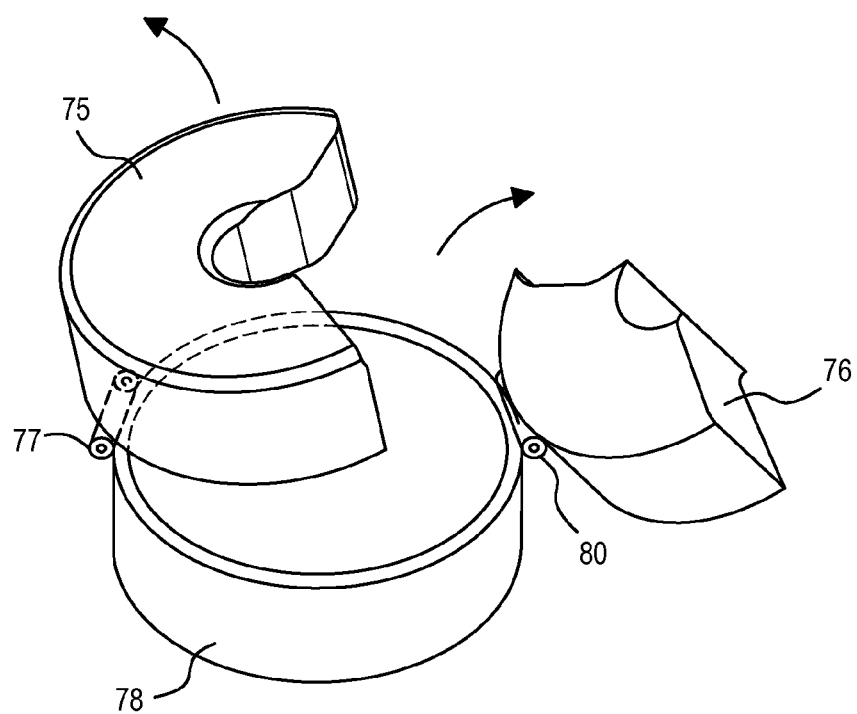

FIG. 19 shows an embodiment wherein the top cover containing the levitation magnets and position sensors is separated into a section 75 and a section 76. Section 75 is attached by a hinge 77 to lower housing 78 so that section 75 rotates upward and away from lower housing 78 to allow insertion of the disposable impeller unit. Section 76 is attached by a hinge 80 to lower housing 78 so that section 76 rotates upward and away from lower housing 78 to allow insertion of the disposable impeller unit. One or both of these hinges may be part of extension arms, making insertion of the disposable impeller unit faster and easier by moving the upper housing section(s) farther away from their common axis. A locking mechanism (not shown) may be provided to lock sections 75 and 76 in place when they are closed over the impeller unit.

Figure 20:
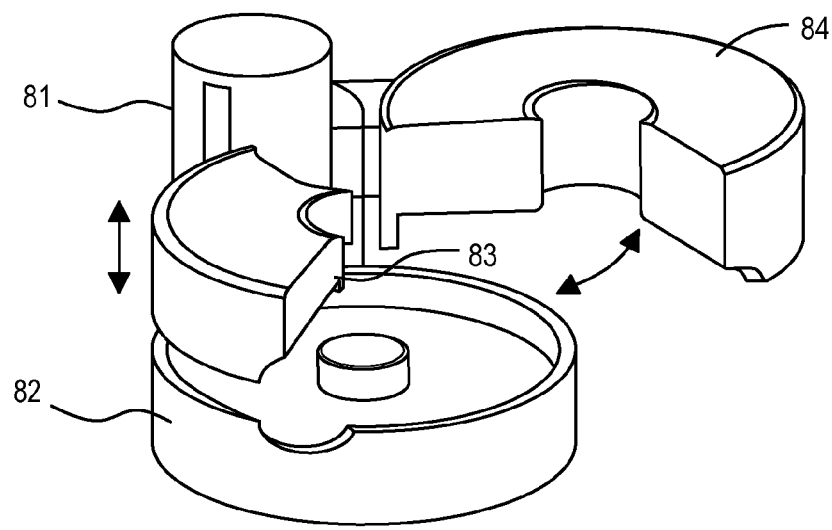

FIG. 20 shows another alternative embodiment wherein a support rod 81 mounted to a lower housing 82 retains a first upper housing section 83 for vertical movement and a second upper housing section 84 for rotational movement.

Figure 21:
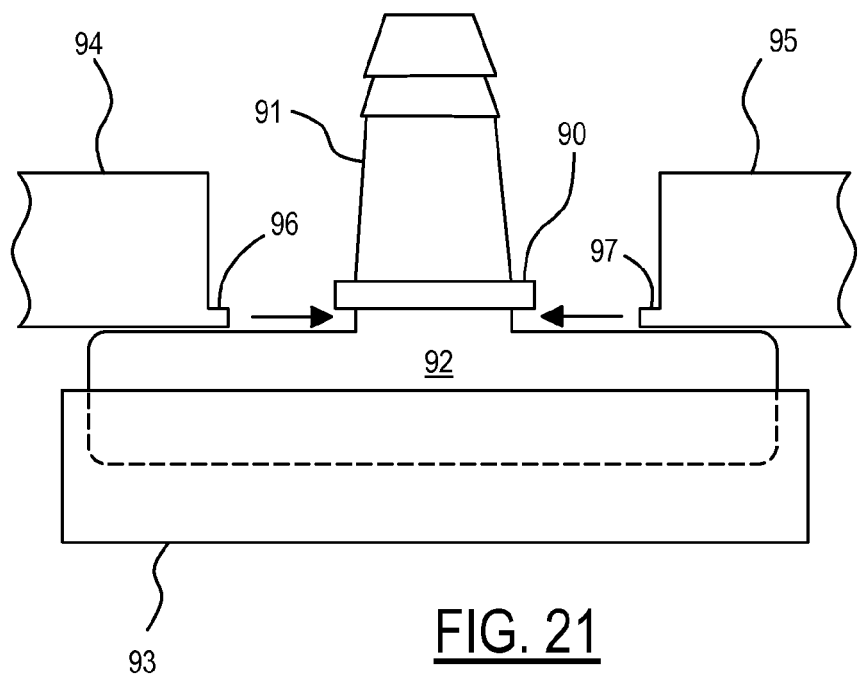

FIG. 21 illustrates an impeller locking feature obtained by providing a flange 90 on inlet port 91 of an impeller unit 92. When impeller unit 92 is placed within lower housing 93 and when upper housing sections 94 and 95 are rotated into a closed position, a pair of tabs 96 and 97 are captured beneath flange 90. Consequently, the top of the impeller unit is constrained from upward and downward movement that could otherwise result from pressure changes within the impeller unit. If allowed to occur, such axial distortion might interfere with the performance of the levitating magnets or position sensors, or with impeller rotation. Similarly related features on the bottom of the impeller unit and also on and/or within the drive unit housing may constrain similar possible movements below the impeller.

What is claimed is:

1. A blood pump comprising:
   a disposable pump head having an inlet and an outlet formed in a sealed impeller housing, the pump head further comprising an impeller contained within the sealed impeller housing having a top disk and a bottom disk with impeller blades mounted therebetween, the top and bottom disks having respective magnetic structures; and
   a re-usable levitation/drive unit having movably coupled upper and lower housing sections, whereby the housing sections are relatively movable to an open position for allowing insertion of the disposable pump head and a closed position for retaining the disposable pump head in a predetermined position, wherein the re-usable levitation/drive unit includes a levitation magnet in one of the housing sections and a drive magnet in the other one of the housing sections;
   wherein the upper housing section comprises first and second jaw elements each relatively movable with respect to the lower housing section, wherein the levitating magnet is located in the upper housing section and comprises a plurality of magnet segments aligned around a periphery of substantially 360° circumferentially, and wherein the first and second jaw elements comprise unequal portions of the circumferential periphery and include unequal numbers of magnet segments, respectively.

2. The blood pump of claim 1 further comprising a plurality of position sensors located in the upper housing section for monitoring levitation of the impeller.

3. The blood pump of claim 1 wherein the first and second jaws are mounted for movement on a support rod.

4. The blood pump of claim 3 wherein at least one of the first and second jaws is hinged from the support rod for sideways movement.

5. The blood pump of claim 3 wherein at least one of the first and second jaws is slidable up and down along the support rod.

6. The blood pump of claim 1 wherein at least one of the first and second jaws is hinged from the lower housing section.

7. The blood pump of claim 1 wherein the sealed impeller housing includes an inlet member aligned with the rotational axis of the impeller and an outlet member tangentially aligned to an outer radial edge of the impeller.

8. The blood pump of claim 7 wherein the impeller includes a central opening for distributing blood from the inlet member to the impeller blades.

9. The blood pump of claim 1 wherein the top disk of the impeller comprises a magnetic sheet for interacting with the levitating magnet.

10. The blood pump of claim 1 wherein the bottom disk of the impeller comprises a plurality of alternating permanent magnetic domains for interacting with the drive magnet.

11. The blood pump of claim 10 wherein each permanent magnetic domain comprises an individual permanent magnet mounted on the bottom disk.

12. The blood pump of claim 10 wherein the permanent magnetic domains comprise respective magnetized areas on a magnetic sheet.

13. The blood pump of claim 1 further comprising a disposable plastic shield mounted to at least one of the upper or lower housing sections.

* * * * *